United States Patent
Haddadi et al.

(10) Patent No.: US 9,671,617 B2
(45) Date of Patent: Jun. 6, 2017

(54) METHOD FOR ESTIMATING A DISTANCE SEPARATING A PAIR OF GLASSES AND AN EYE OF THE WEARER OF THE PAIR OF GLASSES

(71) Applicant: ESSILOR INTERNATIONAL (COMPAGNIE GÉNÉRALE D'OPTIQUE), Charenton-le-Pont (FR)

(72) Inventors: Ahmed Haddadi, Charenton-le-Pont (FR); Jean Delzers, Charenton-le-Pont (FR)

(73) Assignee: ESSILOR INTERNATIONAL (COMPAGNIE GENERALE D'OPTIQUE), Charenton-le-Pont (FR)

( * ) Notice: Subject to any disclaimer, the term of this patent is extended or adjusted under 35 U.S.C. 154(b) by 136 days.

(21) Appl. No.: 14/383,711

(22) PCT Filed: Mar. 8, 2013

(86) PCT No.: PCT/FR2013/000062
§ 371 (c)(1),
(2) Date: Sep. 8, 2014

(87) PCT Pub. No.: WO2014/128361
PCT Pub. Date: Aug. 28, 2014

(65) Prior Publication Data
US 2015/0015848 A1    Jan. 15, 2015

(30) Foreign Application Priority Data
Mar. 8, 2012 (FR) ...................... 12 00704

(51) Int. Cl.
G02C 7/02    (2006.01)
A61B 3/00    (2006.01)
(Continued)

(52) U.S. Cl.
CPC ............ *G02C 7/027* (2013.01); *A61B 3/0008* (2013.01); *A61B 3/113* (2013.01); *A61B 3/14* (2013.01);
(Continued)

(58) Field of Classification Search
CPC .... G02C 13/003; G02C 13/005; G02C 7/027; G02C 7/028; A61B 3/0008; A61B 3/11;
(Continued)

(56) References Cited

U.S. PATENT DOCUMENTS

2010/0128220 A1    5/2010    Chauveau

FOREIGN PATENT DOCUMENTS

| DE | 10 2009 004383 A1 | 7/2009 |
| WO | 2008/009423 A1 | 1/2008 |
| WO | 2008/132356 A1 | 11/2008 |

OTHER PUBLICATIONS

Machine translation of DE 102009004383, retrieved online from espacenet Mar. 11, 2016.*

(Continued)

*Primary Examiner* — Thomas K Pham
*Assistant Examiner* — Cara Rakowski
(74) *Attorney, Agent, or Firm* — Young & Thompson

(57) ABSTRACT

A method for estimating an eye/spectacles distance (VG) includes the steps of:
a) acquiring at least two images of the wearer (1), in which the head (10) of the wearer exhibits various angular positions;
b) determining, for each image acquired, an angle of inclination ($\alpha_{301}$) of the head of the wearer with respect to the image sensor;
c) acquiring at least two simulated values (VG1, VG2, VG3) of the eye/spectacles distance sought;
d) calculating, for each image acquired and with each simulated value, a morphological distance ($EG1_{301}$,
(Continued)

$EG2_{301}$, $EG3_{301}$) between the eye of the wearer and a median plane of the head of the wearer, having regard to the angle of inclination; and e) selecting, from among the simulated values, the one closest to the eye/spectacles distance of the wearer, as a function of the head/plane distances calculated in step d).

13 Claims, 4 Drawing Sheets

(51) Int. Cl.
| | |
|---|---|
| *A61B 3/18* | (2006.01) |
| *A61B 5/11* | (2006.01) |
| *A61B 3/14* | (2006.01) |
| *G02C 13/00* | (2006.01) |
| *A61B 3/113* | (2006.01) |
| *A61B 5/107* | (2006.01) |
| *A61B 3/11* | (2006.01) |

(52) U.S. Cl.
CPC .............. *A61B 3/18* (2013.01); *A61B 5/1121* (2013.01); *A61B 5/1128* (2013.01); *G02C 7/028* (2013.01); *G02C 13/003* (2013.01); *A61B 3/11* (2013.01); *A61B 5/1071* (2013.01); *A61B 5/1072* (2013.01); *A61B 5/1075* (2013.01); *A61B 5/1079* (2013.01)

(58) Field of Classification Search
CPC   A61B 3/111; A61B 3/113; A61B 3/14; A61B 3/145; A61B 5/1121; A61B 5/1128; A61B 5/1079; A61B 5/1075; A61B 5/1072
See application file for complete search history.

(56) References Cited

OTHER PUBLICATIONS

International Search Report, dated Jul. 19, 2013, from corresponding PCT application.

* cited by examiner

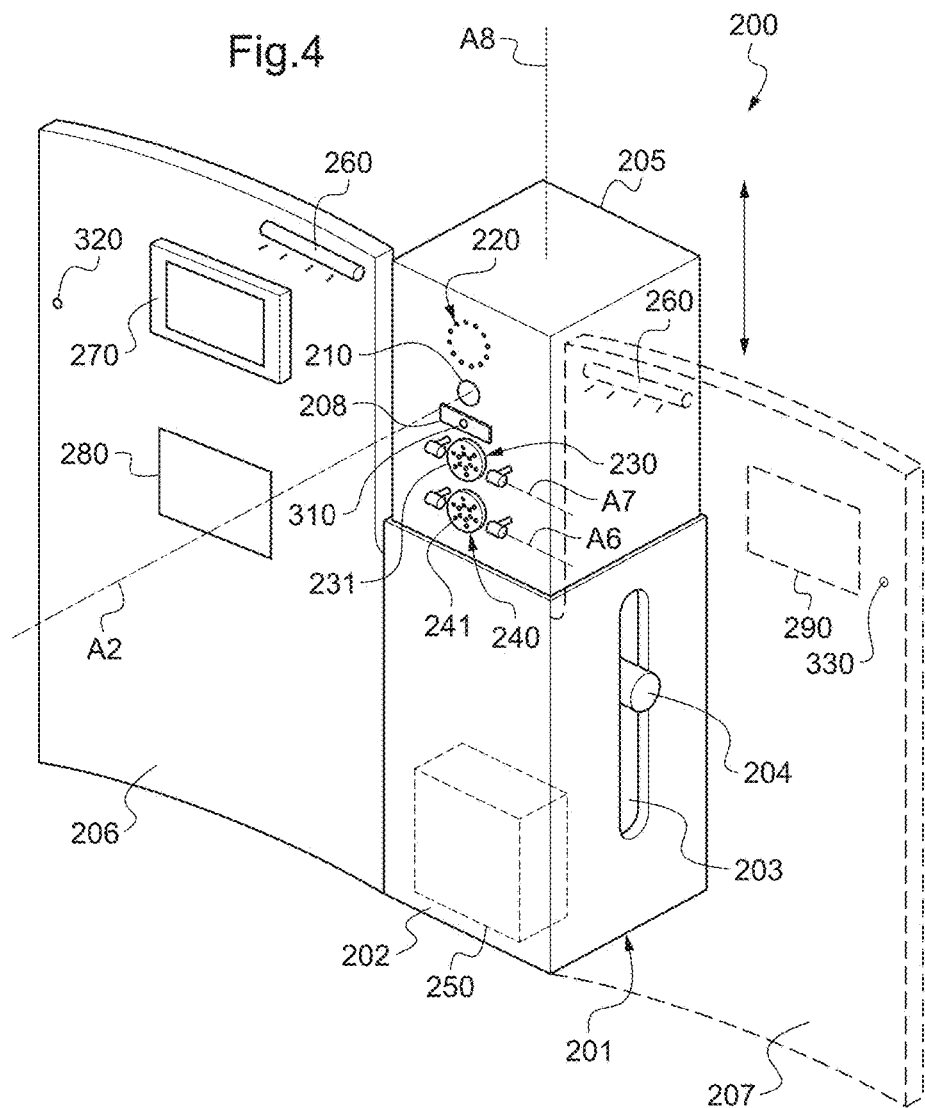

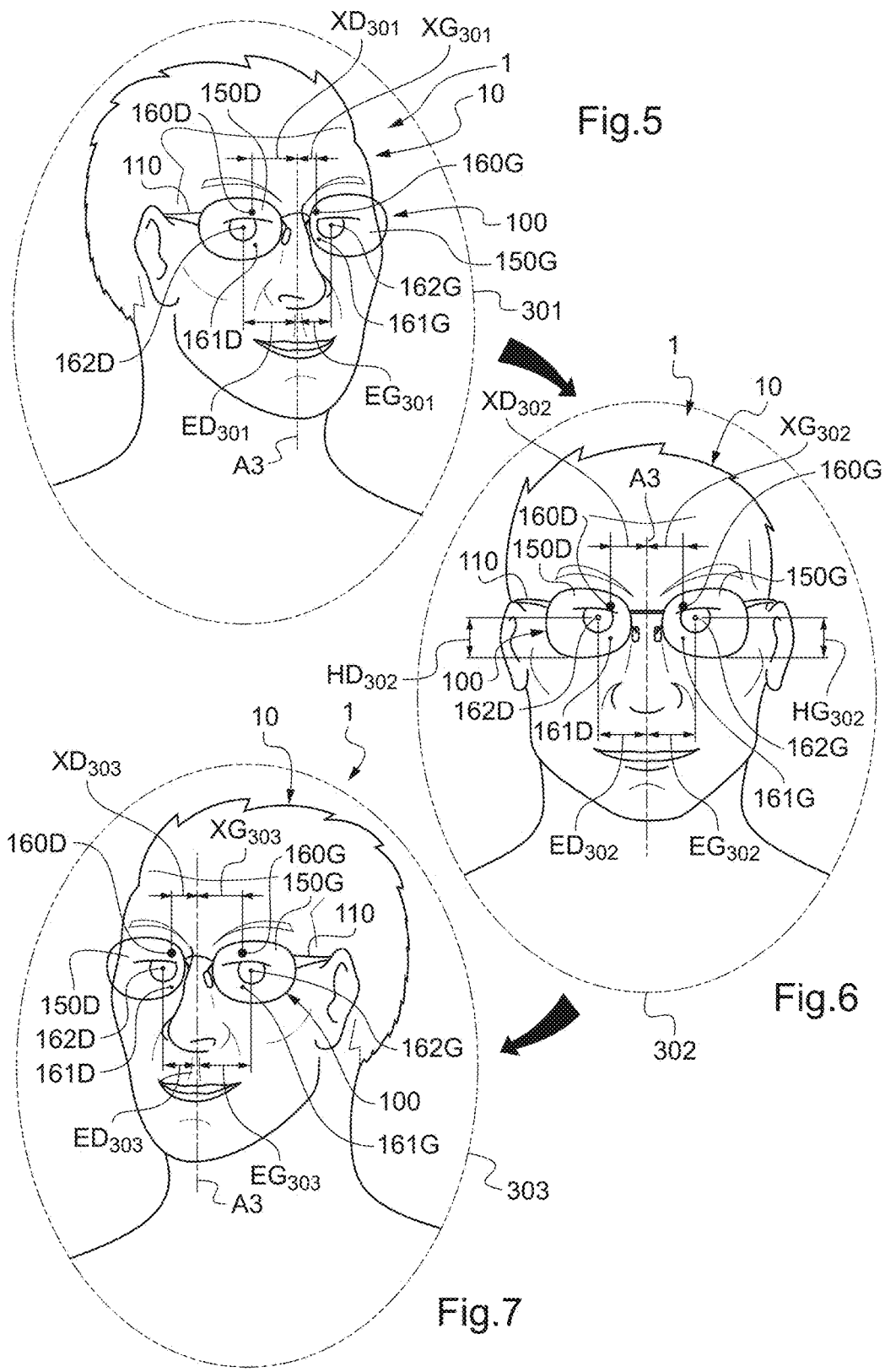

METHOD FOR ESTIMATING A DISTANCE SEPARATING A PAIR OF GLASSES AND AN EYE OF THE WEARER OF THE PAIR OF GLASSES

TECHNICAL FIELD OF THE INVENTION

Generally, the present invention relates to taking measurements of a subject.

It is particularly, but not exclusively, applicable to taking measurements of a spectacle wearer with a view to personalized optical design of corrective ophthalmic lenses tailored to this wearer.

It relates more particularly to a method for estimating an eye/spectacles distance, separating a characteristic plane of a pair of spectacles and a characteristic point of a head of a wearer of said pair of spectacles, comprising steps:

a) of acquisition by an image sensor of at least two distinct images of at least one part of the head of the wearer, in which the head of the wearer exhibits distinct angular positions around a pivoting axis substantially parallel to said characteristic plane and transverse to the optical axis of the image sensor, b) of determination, for each image acquired, of an angle of inclination of the head of the wearer with respect to the image sensor, measured between the optical axis of the image sensor and a plane tied to the head of the wearer which is substantially parallel to said pivoting axis and substantially orthogonal to said characteristic plane, and c to e) of processing of the images to estimate the eye/spectacles distance sought.

It also relates to a device for estimating the eye/spectacles distance, which comprises:

- at least one light source suitable for illuminating the head of the spectacle wearer;
- an image sensor exhibiting an optical axis directed substantially toward the head of the wearer and suitable for acquiring two images of the head of the wearer in which the pair of spectacles illuminated by the light source appears and in which the head of the wearer exhibits two distinct inclinations around the pivoting axis, and
- a calculation unit suitable for processing said images.

PRIOR ART

During the design of a corrective ophthalmic lens, it is sought to take into account many individual geometrico-morphological parameters, called personalized optical design parameters, attributed to the wearer and to the selected spectacle frame, in order to machine the lens such that it is tailored as best as possible to the wearer.

To determine these geometrico-morphological parameters, the optician places the selected spectacle frame on the nose of the wearer and carries out various measurement operations on the wearer thus equipped. Thus he may in particular determine the semi-pupillary distances of the wearer, that is to say the distances between the plane of symmetry of the spectacle frame and each of the wearer's pupils.

These measurements are however falsified when the wearer's face is not exactly opposite the image sensor, and when it thus exhibits a non-zero angle of yaw with respect to the image sensor (the angle of yaw corresponding to the angle formed between the sagittal plane of the wearer's head is the optical axis of the image sensor).

It is indeed understood that when the wearer's head is rotated to the right, the distance measurable in the image acquired between the left eye and the center of the frame will be larger than the wearer's actual left semi-pupillary distance, while the distance measurable between the right eye and the center of the frame will be less than the wearer's actual right semi-pupillary distance.

It is noted more precisely that when the angle of yaw is non-zero, the measurements of the semi-pupillary distances are falsified by about 0.5 millimeter per degree of angle of yaw.

It is then appropriate to measure these semi-pupillary distances not in the plane of the image acquired, but in the midplane of the spectacle frame (which is substantially orthogonal to the arms of the frame when they are unfurled).

A solution then consists in determining the positions in space of the centers of rotation of the wearer's two eyes to deduce therefrom the semi-pupillary distances. Formulated otherwise, knowing the positions of the wearer's pupils in the image acquired, it suffices to determine the distances separating the midplane of the frame from the centers of rotation of the wearer's eyes to deduce therefrom the wearer's semi-pupillary distances.

A procedure for determining the "midplane—centers of rotation of the eyes" distances is set forth in document WO 2008/132356. It consists in equipping the wearer's spectacle frame with a pinpointing system to facilitate the location of the spectacle frame in the image acquired, in asking the spectacles wearer to rotate their head while maintaining their gaze on a fixed point, in taking two shots of the head of the wearer at two different instants, and in geometrically deducing therefrom the distances sought, having regard to the position of the spectacle frame.

This procedure however presents diverse drawbacks.

It is thus necessary to carefully fix the pinpointing system on the spectacle frame, whatever the shape of this frame, this possibly turning out to be tiresome and requiring to be implemented by a trained optician.

The stance of the pinpointing system on the frame may furthermore turn out to be random, depending on the shape of the spectacle frame, and thus falsify the measurements.

It is observed moreover that location of the pinpointing system is difficult to implement automatically and exhibits an appreciable failure rate, so that the optician is often forced to locate this pinpointing system manually in the image acquired.

Finally, the pinpointing system is rather unesthetic, this not being flattering for the spectacles wearer seeing themselves in a mirror and in the image acquired.

SUBJECT OF THE INVENTION

In order to remedy the aforementioned drawbacks of the prior art, the present invention proposes a novel statistical method for estimating a distance separating a given point of the head of the wearer and a given plane of the spectacle frame.

More particularly, there is proposed according to the invention an estimating method such as defined in the introduction, in which provision is made for steps:

c) of acquisition of at least two simulated values of the eye/spectacles distance sought, d) of calculation, for each image acquired and with each simulated value acquired, of a morphological distance between the characteristic point of the head of the wearer and the plane tied to the head of the wearer, having regard to said angle of inclination, and e) of selection, from among the simulated values of the eye/spectacles distance sought, of the value closest to the eye/spectacles distance of the wearer, as a function of the head/plane distances calculated in step d).

Thus, by virtue of the invention, a statistical procedure is used in which, in each image, a simulated value is varied to obtain a corresponding morphological distance, and the simulated value closest to the actual value is selected as a function of the whole set of these morphological distances.

As will be described in detail below, step d) will preferably be based on an iterative trigonometric calculation.

This calculation may of course be carried out otherwise. It could for example be carried out by means of a simple trigonometric calculation, taking into account a significant number of variables (for example the previously measured width and height of each rim of the spectacle frame).

As will be described in detail below, step e) will preferably be undertaken by selecting the simulated value for which the standard deviation between the head/plane distances calculated in step b) is the lowest.

This calculation may of course be carried out otherwise. It could for example be carried out by means of a mathematical function not of standard deviation but rather of variance.

Here, the expression "characteristic point of the eye" is defined as any pinpointable or distinctive point of the eye.

It may be the center of rotation of the eye. As a variant it could of course be the macula or the center of the pupil of the eye.

The "morphological distance" mentioned hereinabove is then defined as the distance between this characteristic point of the wearer's eye and the plane tied to the wearer's head (for example the sagittal plane, or the Frankfurt plane).

The "angular position" of the wearer's head is defined as the angular position of the wearer's head with respect to the image sensor, around a pivoting axis transverse to the optical axis of the image sensor. It then corresponds to the angle formed between the optical axis of the image sensor and the plane tied to the wearer's head (for example the sagittal plane, or the Frankfurt plane).

The "characteristic plane of the pair of spectacles" is defined as a determinable plane of the pair of spectacles. It may for example be the plane which passes through the vertex of the bridge of the frame and which is substantially orthogonal to the unfurled arms of the frame. It could as a variant be the plane which passes through the vertices of the front (or rear) faces of the lenses and which is substantially orthogonal to the unfurled arms of the frame.

The "eye/spectacles distance" is defined for its part as the distance between the characteristic plane of the pair of spectacles and the characteristic point of the eye of the wearer.

The following are other advantageous and nonlimiting features of the method according to the invention:
  in step a), said pivoting axis coincides with the longitudinal axis of the head of the wearer, and in step b), the plane tied to the head of the wearer is parallel to the sagittal plane of the head of the wearer and said angle of inclination is an angle of yaw;
  the characteristic point of the head of the wearer is the center of rotation of one of the two eyes of the wearer, the plane tied to the head of the wearer coincides with the sagittal plane of the head of the wearer, and each morphological distance calculated in step d) is an assumed semi-pupillary distance of the wearer calculated as a function of the position in the image acquired of the position of a corneal reflection reflected by the cornea of said eye of the wearer;
  the position of the plane tied to the head of the wearer is obtained by pinpointing the position of the pair of spectacles in each of the images acquired;
  in step e), for each simulated value, a rate of dispersion of the morphological distances associated with this simulated value is determined, and the simulated value selected is that for which the morphological distances are the least dispersed;
  the rate of dispersion of the morphological distances is a standard deviation;
  there is provided an additional step of estimating the semi-pupillary distance of the wearer, in the course of which the average of the morphological distances associated with the simulated value selected is calculated;
  the device comprising a light source, in step b), said angle of inclination is determined as a function of the position, in each image, of the reflections generated by the light source and reflected by the two lenses of the pair of spectacles;
  said light source is infrared and said image sensor is suitable for acquiring infrared images;
  the characteristic plane of the pair of spectacles is parallel to the midplane of the contours of the lenses of the pair of spectacles;
  said angle of inclination is obtained by installing on the pair of spectacles a pinpointing element having a known geometry, and by determining the position and the shape of said pinpointing element in each image acquired;
  a dimension characteristic of said pair of spectacles is acquired and said eye/spectacles distance of the wearer is scaled as a function of said characteristic dimension acquired.

The invention also relates to a device for estimating an eye/spectacles distance, between a characteristic plane of a pair of spectacles and a characteristic point of a head of a wearer of said pair of spectacles, which comprises:
  at least one light source suitable for illuminating the head of the wearer,
  an image sensor exhibiting an optical axis directed substantially toward the head of the wearer and suitable for acquiring at least two images of the head of the wearer in which the pair of spectacles illuminated by the light source appears and in which the head of the wearer exhibits distinct inclinations around a pivoting axis substantially parallel to said characteristic plane and transverse to the optical axis of the image sensor, and
  a calculation unit suitable for processing said images so as to:
    determine, for each image acquired, an angle of inclination of the head of the wearer with respect to the image sensor, measured between the optical axis of the image sensor and a plane tied to the head of the wearer which is substantially parallel to said pivoting axis and substantially orthogonal to said characteristic plane,
    acquire at least two simulated values of the eye/spectacles distance sought,
    calculate, for each image acquired and with each simulated value acquired, a morphological distance between the characteristic point of the head of the wearer and the plane tied to the head of the wearer, having regard to said angle of inclination, and
    select, from among the simulated values of the eye/spectacles distance sought, the value closest to the eye/spectacles distance of the wearer, as a function of the head/plane distances calculated in step d).

DETAILED DESCRIPTION OF AN EXAMPLE EMBODIMENT

The following description and the appended drawings to which it refers, which are given by way of nonlimiting example, will allow what the invention consists of and how it can be carried out to be understood.

In the appended drawings:

FIG. 4 is a schematic perspective view of a device suitable for implementing the method according to the invention;

FIGS. 5 to 7 show three images acquired by the image sensor in FIG. 3; and

In the following description, certain references consist of a number followed by the letter G or D. These references then respectively designate elements located on the left or right relative to the spectacle wearer. The left and right eyes of the wearer are thus referenced 20G and 20D, respectively.

Figure 1:
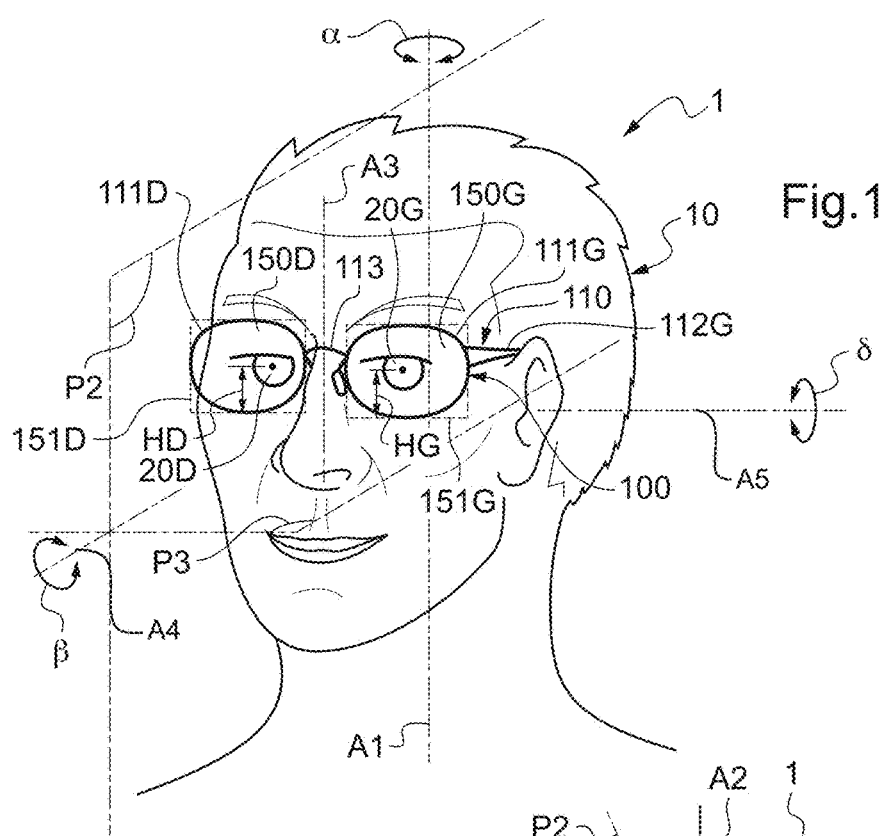
FIG. 1 is a schematic perspective view of the head of a spectacle wearer.

FIG. 1 shows the head 10 of an individual 1 wearing a pair of spectacles 100. This individual will be referred to below in the rest of the description as the "wearer".

In this description, reference will also be made to another individual, who will be referred to as the "vendor" and who will help the wearer 10 choose a pair of spectacles 100 and to measure the data required to manufacture the ophthalmic lenses (not shown) with a view to ordering them and fitting them in the spectacles frame 100 selected by the wearer.

Because the measurements are automated, this vendor does not have to be an optician.

Prior to the measurements, the wearer will choose a pair of spectacles 100 from the pairs of spectacles made available by the vendor.

During the measurements, the wearer will wear this pair of spectacles 100.

Figure 3:
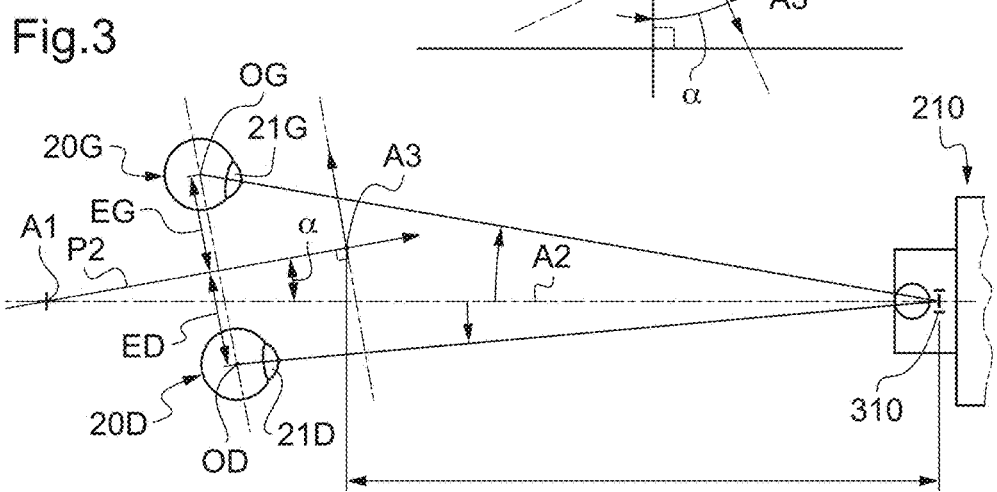
FIG. 3 is a schematic in which the eyes of the spectacle wearer in FIG. 1 and an image sensor are shown.

The wearer will either be sat or stood with their head 10 substantially straight and directed toward an image sensor 210 (see FIG. 3).

The vendor will moreover ask the wearer 1 to look at a target 310 located near the image sensor 210 (see FIG. 3). The centers of the two pupils 21G, 21D and the centers of rotation OD, OG of the two eyes 20G, 20D of the wearer 1 will therefore respectively be aligned with the target 310.

In FIG. 1, it may be seen that the pair of spectacles 100 chosen by the wearer 1 are full-rimmed spectacles (as a variant they could of course be any other type of spectacles, such as half-rimmed or rimless spectacles).

This pair of spectacles 100 comprises a spectacle frame 110 comprising two rims 111G, 111D (or eyewires) in which two demonstration lenses 150G, 150D (intended to be replaced by the ophthalmic lenses tailored to the visual acuity of the wearer) are fitted.

The two rims 111G, 111D are connected to each other via a nose bridge or bridge 113 equipped with two nose pads resting on the nose of the wearer. They are also each equipped with an arm 112G, 112D resting on the corresponding ears of the wearer 1. These arms 112G, 112D each extend rectilinearly over most of their length, along a longitudinal axis, and are curved at their ends.

Each of the two rims 111G, 111D of the spectacle frame 110 has, recessed into its internal side, a groove commonly called a bezel into which is fitted a bevel that protrudes from the edge face of the corresponding demonstration lens 150G, 150D.

Figure 2:
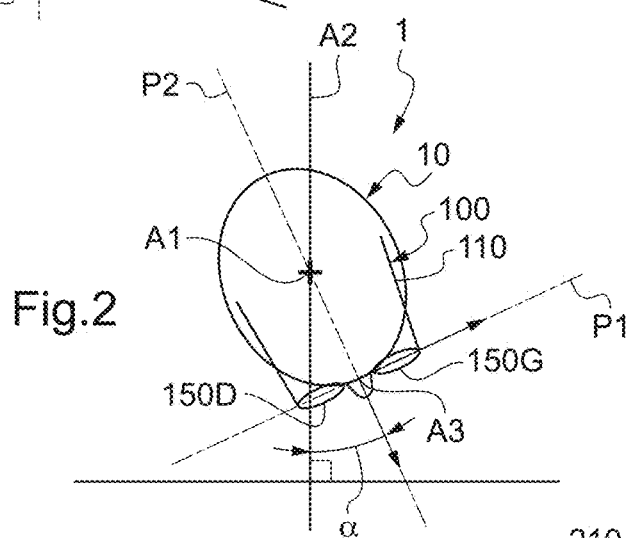
FIG. 2 is a schematic top view of the head of the spectacle wearer in FIG. 1.

As FIG. 2 shows, here a midplane P1 is defined relative to the spectacle frame 110, said midplane passing as close as possible to all of the points on the bottom edge of the bezels of the two rims 111G, 111D.

This midplane P1 is inclined relative to the plane passing through the longitudinal axes of the arms 112G, 112D by an angle called the "pantoscopic angle". On average, the pantoscopic angle of a spectacle frame is about 10 degrees.

As FIG. 1 shows, in each image of the wearer 1 acquired by the image sensor 210, the rims 111G, 111D of the spectacle frame 110 may be pinpointed by means of two boxes 151G, 151D defined according to the "boxing system".

These boxing-system boxes 151G, 151D are defined as rectangles circumscribing the rims 11G, 111D of the spectacle frame 110 (or the demonstration lenses 150G, 150D), two sides of which are vertical and the two other sides of which are horizontal.

Then, in each image, an observable axis A3 of the spectacle frame 100 is defined as being the axis that is parallel to the vertical sides of the boxing-system boxes 151G, 151D, and that is located equidistant from the latter.

As FIG. 1 shows, a Frankfurt plane P3 is defined relative to the wearer 1, in the measuring position, as being the plane passing through the inferior orbital margins and the portion of the wearer (the portion being the highest point in the skull of the ear canal, which corresponds to the tragion of the ear). In the measuring position, this Frankfurt plane P3 will therefore be substantially horizontal.

A sagittal plane P2 is also defined as being the plane orthogonal to the Frankfurt plane P3 and to the axis passing through the centers of rotation OG, OD of the two eyes 20G, 20D of the wearer 1, and passing through the bridge of the nose of the wearer. Therefore, during the measurements, this sagittal plane P2 will be substantially vertical. Its position will be deduced not from the position of the nose of the wearer 1 but rather depending on the position of the pair of spectacles 100 worn by the wearer 1.

A longitudinal axis A1 is defined relative to the head 10 of the wearer 1 as being orthogonal to the Frankfurt plane P3, contained in the sagittal plane P2, and corresponding to the axis of rotation of the head 10 of the wearer 1 when the latter rotates their head from right to left (i.e. when they shake their head to say "no"). In the measuring position, this longitudinal axis A1 will be substantially vertical.

A frontal axis A4 is also defined as being the axis of intersection between the Frankfurt plane P3 and the sagittal plane P2.

A transverse axis A5 is also defined as being the axis perpendicular to the longitudinal A1 and frontal A4 axes.

In the measuring position, these two frontal and transverse axes A4, A5 will be substantially horizontal.

As FIG. 3 shows, the semi-pupillary distances EG, ED of the wearer 1 are defined as the distances separating the sagittal plane P2 from the centers of rotation OG, OD of the two eyes 20G, 20D of the wearer 1.

As FIG. 1 shows, the pupillary heights HG, HD of the wearer are for their part defined as the distances separating, in each acquired image, the centers of rotation OG, OD of the eyes 20G, 20D of the wearer 1 (which in practice are coincident in the image with the centers of the pupils 21G, 21D of the wearer 1) and the lower edge of the corresponding boxing-system box 151G, 151D.

Such as shown in FIG. 3, a horizontal plane and a vertical plane are moreover defined relative to the image sensor 210, the intersection of these planes being coincident with the optical axis A2 of the image sensor 210. Ideally, it is then sought to place the head 10 of the wearer 1 so that its Frankfurt plane P3 is coincident with the horizontal plane of the image sensor 210 and so that its sagittal plane P2 is coincident with the vertical plane of the image sensor 210.

In practice, a slight offset between these planes, liable to corrupt the measurements, is generally observed.

This offset may be measured by means of three angles, namely roll angle β, pitch angle δ and yaw angle α, which correspond to the three ways in which the head 10 of the wearer 1 is free to pivot.

Thus, the yaw angle α will be defined as the angle of pivoting of the head 10 of the wearer 1 about the longitudinal axis A1, between the ideal position of the head 10 of the wearer (facing the optical axis A2) and the actual position of the head 10 of the wearer. This yaw angle α will be measured in the horizontal plane of the image sensor 210.

The roll angle β will be defined as the angle of pivoting of the head 10 of the wearer 1 about the frontal axis A4 between the ideal position of the head 10 of the wearer and the actual position of the head 10 of the wearer. This roll angle β will be easily measurable on each acquired image, depending on the inclination of the observable axis A3.

The pitch angle δ will be defined as the angle of pivoting of the head 10 of the wearer 1 about the transverse axis A5, between the ideal position of the head 10 of the wearer (facing the optical axis A2) and the actual position of the head 10 of the wearer. This pitch angle δ will be measured in the vertical plane of the image sensor 210.

FIG. 4 shows the device 200 that allows the method according to the invention to be implemented and that, more generally, allows the data required to order the ophthalmic lenses to be fitted in the spectacle frame 110 selected by the wearer 1, in place of the demonstration lenses 150G, 150D, to be measured and acquired.

This device takes the form of a spectacle kiosk 200, simultaneously playing the role of a spectacle frame display and a measuring center.

For this purpose it comprises at least one chassis 201, a light source 220, 230, 240, an image sensor 210 and a calculation unit 250.

Preferably, the light source 220, 230, 240 emits in the infrared and the image sensor 210 captures infrared images.

The domain of the infrared that will be used here is the near infrared, the wavelengths of which are comprised between 780 and 1400 nm.

Specifically, using infrared light has a number of advantages. It especially allows parasitic reflections resulting from exterior or interior light that reflects on the demonstration lenses 150G, 150D of the pair of spectacles 100 to be avoided. It also makes it possible to prevent the wearer 1 from being dazzled during the measurements. Lastly, it makes it possible for the eyes of the wearer 1 in the images acquired by the image sensor 210 to be seen even when the demonstration lenses 150D, 150G are tinted.

The chassis could be a single part, such that the image sensor and the light sources are held immobile relative to the floor on which the spectacle kiosk stands. In this case, it would be necessary to provide a height adjustable stool so as to be able to place the wearer such that their head enters the field of the image sensor.

In contrast, in the embodiment of the kiosk 200 shown in FIG. 4, the chassis 201 comprises a foot 202 that is placed on the ground, and a slide 205 that is mounted so as to move translationally relative to the foot 202 along a vertical axis A8 and that bears the light sources 220, 230, 240 and the image sensor 210.

The position of the image sensor 210 is thus adjustable in height depending on the size of the wearer 1.

The foot 202 more precisely has a hollow parallelepipedal shape that is elongate along the vertical axis A8 and that has a square horizontal cross section.

This foot 202 has a lower end that is closed by a wall placed on the ground, and an open upper end via which the slide 205 is inserted.

For this purpose, this slide 205 has a hollow parallelepipedal shape, with a horizontal cross section of outside dimensions equal to the inside dimensions of the foot 202, thereby allowing it to slide in the foot 202.

This slide 205 has a lower end that is open to the interior of the foot 202, and an upper end that is closed by a flat wall.

The slide 205 has, on two opposite sides, two protruding pins 204 that are inserted into two vertical oblong holes 203 produced in two opposite sides of the foot 202, in order to allow the slide 205 to be guided translationally along the vertical axis A8, between two (high and low) stop positions.

Provision is moreover made for motorized actuating means (not shown) allowing the slide 205 to be raised and lowered in the foot 202 to the desired height.

Provision is also made for means (not shown) for determining the height of the slide 205 in the foot 202 (for example an encoder wheel associated with a rack).

The chassis 200 moreover has two lateral wings 206, 207 that border its front face turned toward the wearer 1.

These two lateral wings 206, 207 are formed by vertical walls that are slightly curved forward and that are mounted on hinges on the two opposite sides of the foot 202 in which the vertical oblong holes 203 are provided.

The front faces of these wings 206, 207 are moreover equipped with hooks (not shown) on which the spectacle frames from which the wearer makes his/her choice rest.

In FIG. 4, it may be seen that the slide 205 bears at least two (here three) infrared light sources 220, 230, 240 suitable for illuminating the head 10 of the wearer 1 in the measuring position.

These light sources 220, 230, 240 are preferably distributed on either side of the image sensor, in the vertical plane of the image sensor 210.

These three light sources 220, 230, 240 are here mounted so as to be translationally immobile relative to the slide 205 and are formed of a plurality of light-emitting diodes (LEDs).

One of the light sources, called the main source 220, is located a small distance away from the image sensor 210 (i.e. here less than 10 centimeters from the image sensor). It is composed of a plurality of LEDs distributed in a circle. These LEDs are fastened directly to the slide 205. Such as shown in FIG. 4, this main source 220 is located above the image sensor 210.

The two other light sources, called secondary sources 230, 240, are located one above the other below the image sensor 210. They are each composed of a number of LEDs that is equal to the number of LEDs used in the main source 220, these LEDs being distributed in two concentric circles. They emit light of lower intensity than the intensity of the light emitted by the main source 220. The light intensities emitted by the secondary sources 230, 240 are, in the same way as the intensity emitted by the main source 220, adjustable.

These two secondary sources 230, 240 are fastened to bases 231, 241 that are mounted so as to be able to move rotatably relative to the slide 205 about two separate horizontal axes of rotation A6, A7. By virtue of this mobility, it is possible to manually direct these secondary sources 230, 240 toward the head 10 of the wearer 1.

The three light sources 220, 230, 240 are more precisely designed to form separate reflections on the demonstration lenses 150G, 150D of the pair of spectacles 100 worn by the wearer 1.

Thus, when all the light sources 220, 230, 240 are reflected on the two demonstration lenses 150G, 150D, the image sensor 210 may observe six glass-reflections.

Using three light sources 220, 230, 240 allows the image sensor 201 to see at least some of these reflections whatever the pitch angle δ of the head of the wearer 1. Specifically, it will be understood that when the wearer 1 inclines their head forward, the reflections seen by the image sensor 210 rise up and eventually leave the demonstration lenses 150G, 150D.

The three light sources 220, 230, 240 moreover form a single reflection on each eye of the wearer 1, called the corneal reflection.

FIG. 6 shows a situation in which only two of the three light sources 220, 230, 240 reflect on the two demonstration lenses 150G, 150D. Thus, four glass-reflections 160G, 160D, 161G, 161D, generated by the main source 220 and one of the secondary sources 230, and two corneal reflections 162G, 162D are observed on the two demonstration lenses 150G, 150D. On the other hand, the third light source 240 is too low, having regard to the pitch angle δ of the head of the wearer 1, to generate reflections on the demonstration lenses 150G, 150D.

Of course, as a variant, provision could be made for the kiosk to comprise only one single infrared light source.

The latter could be immovably mounted in a predetermined position relative to the image sensor. It will then be preferable to use a light source that is quite large in size to generate a detectable corneal reflection. Moreover, this light source will have to be placed such that the two glass-reflections that it generates are located substantially halfway up the demonstration lenses 150G, 150D (i.e. on the axis passing through the centers of the two boxing-system boxes of the frame) when the head 10 of the wearer 1 is ideally placed (Frankfurt plane P3 coincident with the horizontal plane of the image sensor 210 and sagittal plane P2 coincident with the vertical plane of the image sensor 210), taking into account the frame-average pantoscopic angle.

Thus, it will be recommended to check, during the measurements, that the pitch angle of the head of the wearer remains small, so that the image sensor can see the reflections of this light source on the demonstration lenses.

According to another variant, provision will possibly be made for this single light source to be mounted so as to be translationally movable vertically relative to the image sensor, in order to compensate for the pitch angle of the head of the wearer.

Such as shown in FIG. 4, the kiosk 200 here comprises one single image sensor 210 with a horizontal optical axis A2.

Here, this image sensor is formed by a video camera 210 suitable for acquiring images in the near infrared and in the visible.

Here, this video camera is the Sony® video camera referenced: FCB-EX490. It is equipped with an infrared filter that can be switched between a normal position in which the latter filters infrared light so that the video camera 210 can acquire an image in the visible domain (called the "visible image" below), and a retracted position in which it allows infrared light to pass to the sensor, which can then acquire an image in the infrared domain (called the "infrared image" below).

This video camera is thus suitable for acquiring infrared images of the wearer, in which the glass-reflections and corneal reflections clearly appear, and visible images of the wearer allowing the latter to check that the selected pair of spectacles 100 suits him/her.

Of course, as a variant, provision will possibly be made not for just one video camera, but for two separate video cameras, one suitable for acquiring infrared images and the other suitable for acquiring visible images.

Here, the front wall of the slide 205 contains a window closed by a one-way mirror, behind which the video camera 210 is located. Thus, the video camera 210 cannot be seen from the exterior of the kiosk 200, but it remains suitable for acquiring images of individuals placed in front of the kiosk 200.

The video camera 210 is then installed in the kiosk 200 such that its objective is located making contact with or near to the back face of this one-way mirror.

The objective of the camera 210 is moreover encircled by an opaque sidewall that prevents parasitic reflections from appearing in the acquired images.

In the present instance, all of the video camera is here housed in an opaque housing that is open to the front via an aperture through which the objective emerges, this housing being located in contact with the back face of the one-way mirror.

The spectacle kiosk 200 moreover comprises at least one target 310 located beside and a small distance away from the objective of the video camera 210, such that it may be seen by the wearer 1 in the measuring position.

Here, this target 310 comprises a window 208 produced in the wall of the slide 205, between the objective of the video camera 210 and the secondary sources 230, 240, through which an LED may be seen. In practice, this LED is here located in the foot 202 of the chassis 200 and is reflected toward the window 208 by means of a set of mirrors.

This target 310 allows the gaze of the wearer 1 to be drawn toward the objective of the video camera 210 during the measurements.

Provision is also made for two additional targets 320, 330, located on the exterior edges of each of the wings 206, 207 of the chassis 200, in the horizontal plane of the video camera 210.

As will be described in greater detail in the rest of this text, these additional targets 320, 330 will allow the gaze of the wearer 1 to be drawn in sequence toward one side of the kiosk 200 and then the other, in order to determine whether this wearer 1 has a propensity to turn their gaze by moving rather their head 10 or their eyes 20G, 20D.

Provision is moreover made for two neon tubes 260, positioned on the upper edges of the two wings 206, 207 of the chassis 200, respectively, which illuminate the head 10 of the wearer 1 such that the visible images acquired by the video camera 210 are adequately exposed.

Provision is also made, in one of these two wings 206, for means for displaying 270 and means for printing 280 the visible images acquired.

Here, the displaying means consist of a touchscreen 270 fastened to the front face of the wing 206, so as to be visible to the wearer 1 in the measuring position.

As for the printing means, they are designed to print out sheets summarizing order data for ophthalmic lenses, on which the photos of the wearers appear.

Provision is moreover made for means for scanning the prescriptions of the wearer 1.

Here, the printing means and the scanning means are merged into one and consist of a single multifunction color printer 280 located in a housing provided recessed into the front face of the wing 206 of the chassis 200.

Of course, as a variant, it would also be possible to provide two separate apparatuses, one for printing the summarizing sheets and the other for scanning the prescriptions.

Lastly, provision is made, on the other of the two wings 207, for a means for acquiring at least one dimension of the pair of spectacles 100. Specifically, the images acquired by the video camera 210 do not allow the dimensions of the pair of spectacles 100 of the wearer 1 to be determined. Thus, it is necessary to scale the acquired images.

The aforementioned acquiring means 290 may take various forms.

Preferably, they comprise a barcode reader 290 connected to a database each record of which is associated with a spectacle frame model and comprises an identifier and data relating to this spectacle frame model.

In the present instance, the identifier of each record is formed by the number of the barcode that is assigned to the spectacle frame model.

As for the data memorized in each record, here they include:
- the total width of the spectacle frames of the model in question, measured between the two arms 112D, 112G;
- the ratio between the height and the width of the boxing-system boxes 151G, 151D of the rims of these spectacle frames; and
- the distance separating these two boxing-system boxes 151G, 151D.

Of course, the data memorized in each record of the database could include a smaller number of elements (for example only the total width of the spectacle frame) or a larger number of elements (for example the exact shape of the rims, the material of the spectacle frames, the pantoscopic angle and the curvature of the spectacle frames, etc.).

As a variant, these acquiring means could comprise only a simple keyboard (a physical keyboard or a keyboard displayed on the touchscreen) allowing the vendor:
- to input the width of the selected spectacle frame 110, which he or she will have measured beforehand using a ruler; and
- to position, on the acquired image, two cursors at the two points between which he or she measured the width of the frame.

As yet another variant, these acquiring means could comprise only a simple gauge of known dimensions, to be attached to the selected spectacle frame (by clip fastening, adhesive bonding or any other means), in order to obtain, in each image acquired by the video camera, a model the dimensions of which are known, thus allowing this image to be scaled.

As FIG. 4 shows, the calculation unit 250 of the spectacle kiosk 200 is for its part housed in the foot 202 of the chassis 200. It is designed to control the various electronic components of the kiosk 200 and to process the images acquired by the video camera 210.

For this purpose, this calculation unit 250 comprises a processor (CPU), a random access memory (RAM), a read-only memory (ROM), analog to digital (A/D) converters and various input, output and communications interfaces.

By virtue of its input interfaces, the calculation unit 250 is suitable for receiving the images acquired by the video camera 210, the height of the slide 205 in the foot 202, measured by said determining means, and the barcode number of the selected spectacle frame, read by the barcode reader 290.

Thus, the calculation unit 250 continuously stores these various data in its random access memory.

By virtue of a software program stored in its read-only memory, the calculation unit 250 is suitable for implementing all of the method that will be described in the rest of this description. Thus, it is for example suitable for generating signals for controlling the means for actuating the swing 205 in order to position the latter at the desired height, and communications signals containing data for ordering ophthalmic lenses.

By virtue of its output interfaces, the calculation unit 250 is suitable for transmitting these output signals to the various electronic components of the kiosk 200, especially to the video camera 210, to the light sources 220, 230, 240, to the touchscreen 270, to the multifunction printer 280, to the targets 310, 320, 330 and to the means for actuating the slide 205.

By virtue of its communications interfaces, the calculation unit 250 is suitable for transmitting the communications signals to an ophthalmic lenses manufacturing center.

Lastly provision is made for a switch for powering up the kiosk 200.

Before the arrival of the wearer 1, the vendor powers up the kiosk 200 using the switch provided for this purpose.

During power-up, the control unit controls the electrical power supply of the neon tubes 260 so as to illuminate the pairs of spectacles that are on display on the wings 206, 207 of the chassis 201 of the kiosk 200.

As for the three infrared light sources 220, 230, 240, they remain turned off.

Next, when an individual presents themselves, after having read a message on the screen inviting them to do so, he or she chooses a pair of spectacles 100 from all of those that are on display on the wings 206, 207 of the chassis 201 of the kiosk 200. In the example shown in the figures, the selected pair of spectacles is full-rimmed. Next, as invited to do so by a message displayed on the screen, the individual calls the vendor for the rest of the protocol.

Next, provision is made for an operation for determining a characteristic dimension of the selected spectacle frame 110.

As was described above, this operation is especially provided in order to allow the acquired images to be scaled.

During this operation, the vendor passes the barcode of the selected spectacle frame 110 in front of the barcode reader 290. The calculation unit 250, by virtue of the barcode number, then searches in the database for the record corresponding to this spectacle frame 110, then it recovers and stores in its read-only memory the following data: the total width of the spectacle frame 110, the ratio between the height and the width of the boxing-system boxes 151G, 151D of the rims 111D, 111G of this spectacle frame 110, and the distance separating these two boxing-system boxes 151G, 151D.

Of course, as was described above, this barcode-reading operation could be replaced by a simpler operation consisting, for the vendor, in measuring the total width of the spectacle frame using a ruler, in inputting said width on a virtual keyboard displayed on the touchscreen, and in positioning on the acquired image two cursors at the two points between which the vendor measured the width of the frame (this operation for positioning the two points possibly as a variant being carried out automatically).

Provision is then made for an operation for acquiring prescriptions of the wearer 1 that the latter will have obtained beforehand at an optometrist.

These prescriptions are generally written on a prescription form and in particular include the type of lenses (single-vision, bifocal, progressive, tinted, etc.) and the refringent power that the lenses must have to correct the visual deficiencies of the wearer (i.e. their spherical, cylindrical and prismatic optical powers and their cylinder axes). They may of course include other information such as, in the case of bifocal or progressive lenses, an addition.

During this operation then, the vendor takes the prescription form and scans it using the multifunction printer 280 so that the calculation unit 250 can store the scanned image of this prescription form in its read-only memory.

The vendor may also ask the wearer to choose the treatments that they would like on their ophthalmic lenses (antireflection, hydrophobic, etc.) and input this information into fields displayed for this purpose by the calculation unit 250 on the touchscreen 270.

Once this information has been acquired, the calculation unit 250 powers up the first target 310.

It also displays on the touchscreen 270:
a message indicating that the measuring operations may commence;
images acquired "in real time" by the video camera 210; and
two arrows oriented in opposite directions, one pointing up and the other pointing down, for moving the slide 205 up or down.

The vendor then firstly invites the wearer 1 to put on their spectacles and to keep them on during all of the examinations that follow.

As will be described in detail in the rest of this description, these examinations will then allow the kiosk 200 to determine the semi-pupillary distances EG, ED and the pupillary heights HG, HD of the wearer 1, and advanced personalization parameters such as the distance VG, VD between the spectacle frame 110 and each eye of the wearer 1 (FIG. 8), the mobility behavior of their gaze, etc.

To do this, the vendor asks the wearer 1 to place themselves facing the kiosk 200, in the measuring position, and to look at the first target 310 while keeping their head straight, such that its Frankfurt plane P3 is substantially horizontal and its sagittal plane P2 is substantially vertical.

Here, the wearer 1 is invited to place themselves standing facing the slide 205 of the chassis 201 of the kiosk 200.

The vendor then adjusts the position of the slide 205 to a height suitable for the height of the wearer 1. For this purpose, he or she uses the arrows displayed on the touchscreen 270 to control the upward or downward motion of the slide 205 until it is at a height such that all of the face of the wearer 1 appears in the images acquired by the video camera 210 and displayed on the touchscreen 270.

Thus, in this position, all of the face of the wearer 1 is contained in the field of the video camera 210.

This operation for positioning the video camera 210 to the height of the head 10 of the wearer 1 could of course be carried out in another way.

Thus, it could be carried out automatically by the calculation unit, which would process the images acquired by the video camera so as to pinpoint therein the spectacle frame, and which would control the swing accordingly to a height such as to site the spectacle frame at the center of the images acquired by the video camera.

As a variant, if the image sensor is not movably mounted relative to the ground, this positioning operation will possibly be carried out by asking the wearer to sit on a stool the height of which will have been adjusted beforehand.

Once this operation for positioning the wearer 1 relative to the video camera 210 has been carried out, the vendor initiates the taking of measurements by pressing on an ad hoc button displayed on the touchscreen 270.

The control unit 250 then turns on the three infrared light sources 220, 230, 240, to a nominal intensity.

Of course, the control unit could modulate this intensity, depending on the intensity of outside light, in order to prevent the latter from disrupting the measurements. However, using infrared light allows these disruptions to be limited, to the point that the nominal intensity is generally sufficient.

The use of three distinct light sources 220, 230, 240 then ensures the presence of at least one reflection on each demonstration lens 150G, 150D of the pair of spectacles 100, provided of course that the wearer 1 does not divert their head completely.

In the variant where the kiosk comprises only one light source movable heightwise relative to the video camera, the operation for positioning the wearer facing the video camera would follow an automatic operation for positioning the light source. During this operation, the calculation unit would vary the height of the light source and would process the images acquired by the video camera in order to immobilize the light source at the height at which the glass-reflections are centered on the demonstration lenses.

Whatever the case may be, the vendor then asks the wearer 1 to turn their head 10 from right to left and from left to right, about the longitudinal axis A1 (so as to shake their head to say "no").

He or she is told that the movement must be made slowly (with a period longer than one second), with a small amplitude (about 10 degrees).

As a variant, provision could be made to mount the video camera and the light sources movably so that they pivot together about the longitudinal axis of the head of the wearer. Thus, the wearer would not have to move their head.

Next, when the wearer 1 starts turning their head in the requested way, the vendor presses on a button for initiating the measurements, said button being displayed on the touchscreen 270.

The video camera then acquires a plurality of infrared images, on which the head 10 of the wearer 1 and their pair of spectacles 100 appear.

The acquired images are first stored in the random access memory of the calculation unit 250. Certain of the images, judged to be usable, are then selected by the calculation unit 250 and stored in its read-only memory. The selection of the acquired images is carried out in the following way.

An acquired image may contain a plurality of glass-reflections (6 at most), each glass-reflection 160G, 160D, 161G, 161D is scored individually on various criteria, especially on its:
shape (width, height, width/height ratio); and
intensity (luminance).

Each pair of reflections (generated by a given light source and reflected by the two demonstration lenses, respectively) is moreover scored according to other criteria, especially:
the distance between the reflections;
their horizontality relative to the horizontal axis of the boxing-system boxes; and
by comparison of the areas of the reflections.

Here, the score attributed to each criterion is not binary. Provision may for example be made for it to vary continually between 0 and 1 such that:

it is equal to 1 if the criterion is comprised between 90% and 110% of its nominal value (predetermined and stored in the read-only memory of the calculation unit 250);

it is equal to 0 if the criterion is higher than 120% or lower than 70% of its nominal value; and it varies linearly between 70% and 90% and between 110% and 120%.

The criteria applied to the glass-reflections may also apply mutatis mutandis to the corneal reflections 162G, 162D. An additional criterion applying to the corneal reflections will be the distance separating each corneal reflection from the observable axis A3.

Thus, the chance of an image being selected increases with the product of the scores attributed to the various aforementioned criteria.

Provision may for example be made for the images selected to be those for which the product of the scores is higher than a predetermined threshold.

As a variant, provision may be made for the images selected to be those for which the products of the scores are the highest.

Moreover, provision may be made for an image to be automatically rejected if one of the scores attributed to it is lower than another predetermined threshold.

Thus, if, in an acquired image, the wearer 1 has their head turned by too large a yaw angle α and the glass-reflections are no longer present within the contour of the demonstration lenses 150G, 150D, this image is automatically rejected.

Moreover, if, in an acquired image, the wearer 1 has their head inclined by too large a roll angle β and the glass-reflections generated by a given light source are offset in height on the two demonstration lenses, this image will possibly be rejected if this offset is truly too large, or selected if the scores attributed to the other criteria are high.

The calculation unit 250 thus obtains a limited number of infrared images usable in the rest of the method.

In this description, for the sake of clarity, the calculation unit 250 will be considered to have selected only three infrared images 301, 302, 303—shown in FIGS. 5 to 7.

Preferably, the calculation unit will stop the image acquisition when it has selected at least 10 different images.

Next, the calculation unit 250 switches the infrared filter of the video camera 210 in order to store a visible image of the face of the wearer 1.

It simultaneously turns the infrared light sources 220, 230, 240 off and displays a message on the touchscreen 270 indicating to the wearer that he or she can stop turning their head.

This message is therefore displayed after the calculation unit 250 has selected a predetermined number of images, here equal to 10.

As a variant, provision could be made to display this message after a predetermined length of time, for example equal to 10 seconds, deemed to be long enough to allow a large enough number of usable images to be obtained. The images could then possibly be selected subsequently, after all the images have been acquired.

Once the images 301, 302, 303 have been selected, the calculation unit 250 calculates the yaw angle α of the head 10 of the wearer 1 in each of these images.

This yaw angle α is calculated by locating, in each image 301, 302, 303, the glass-reflections 160D, 160G, 161D, 161G relative to the sagittal plane P2 of the head of the wearer 1.

Here, this yaw angle α is more precisely determined by locating the glass-reflections 160D, 160G, 161D, 161G relative to the observable axis A3 of the spectacle frame (since its position substantially corresponds to the intersection of the sagittal plane P2 with the midplane P1 of the spectacle frame 110).

The position of the observable axis A3 of the spectacle frame 110 is obtained in 3 steps, consisting in:

pinpointing in each image 301, 302, 303 the spectacle frame 110, and especially the rims 111D, 111G of this spectacle frame;

positioning on each image 301, 302, 303 the boxing-system boxes 151G, 151D; and determining the position of the axis passing between these two boxing-system boxes, which in practice corresponds to the observable axis A3.

Here, using infrared light makes it easier to pinpoint the spectacle frame 110, the contour of which stands out clearly from that of the face of the wearer 1.

Thus, the yaw angle α of the head 10 of the wearer 1 in each image 301, 302, 303 is calculated as a function of the distances separating the glass-reflections 160D, 160G, 161D, 161G from the observable axis A3.

Typically, as FIGS. 5 to 7 clearly show, the calculation unit 250 determines in each image 301, 302, 303 the distances $XD_{301}$, $XG_{301}$, $XD_{302}$, $XG_{302}$, $XD_{303}$, $XG_{303}$ separating the observable axis A3 from the centers of the two largest glass-reflections 160G, 160D (the glass-reflections generated by the secondary sources being used only if the glass-reflections generated by the main source do not appear on the acquired images).

The yaw angle $α_i$ of the head 10 of the wearer 1 in each image 301, 302, 303 is then determined in the following way:

$α_i = k \cdot (XG_i - XD_i)/(XG_i + XD_i)$, with $i$ ranging from 301 to 303.

The coefficient k is then a constant relating to the curvature of the spectacle frame.

This coefficient k will possibly be formed by a predetermined and invariable constant, stored in the read-only memory of the calculation unit 250. It will therefore always be the same whatever the spectacle frame selected by the wearer. This coefficient k will then possibly be determined experimentally on the basis of a representative sample of spectacle frames, and thus chosen to be equal to about 40°.

As a variant, this coefficient k will possibly be formed by a predetermined constant associated with the spectacle frame selected by the customer. In this variant, this coefficient k will then be determined experimentally for each spectacle frame model, then stored in the database so as to be accessible during the calculation of the yaw angle $α_i$ of the head 10 of the wearer 1.

This yaw angle could possibly be determined in another way.

By way of example, provision could be made to equip the spectacle frame with a pinpointing system comprising easily pinpointable geometric features separated by a known real distance, and to determine the yaw angle as a function of the distance separating these geometric features in the acquired image (set beforehand to a 1:1 scale). Such a method is described in detail in document WO 2008/132356.

At this stage, the calculation unit 250 has, stored in its memory, the yaw angles $α_{301}$, $α_{302}$, $α_{303}$ of the head 10 of the wearer 1 in each selected image 301, 302, 303.

The calculation unit then determines the semi-pupillary distances EG, ED of the wearer 1 as a function of the positions of the corneal reflections 162G, 162D of the wearer 1 in at least one of the selected images 301, 302, 303.

The procedure according to the invention consists in considering all the images 301, 302, 303 selected, and then, by a statistical procedure, in evaluating the semi-pupillary distances EG, ED of the wearer 1.

This statistical procedure not only allows the semi-pupillary distances EG, ED of the wearer 1 to be evaluated, but also the eye/spectacles distances VG, VD separating the midplane P1 of the spectacle frame 110 and the centers of rotation OG, OD of the eyes 20G, 20D of the wearer 1.

This statistical procedure is then implemented on one of the two eyes 20G, 20D of the wearer 1.

Figure 8:
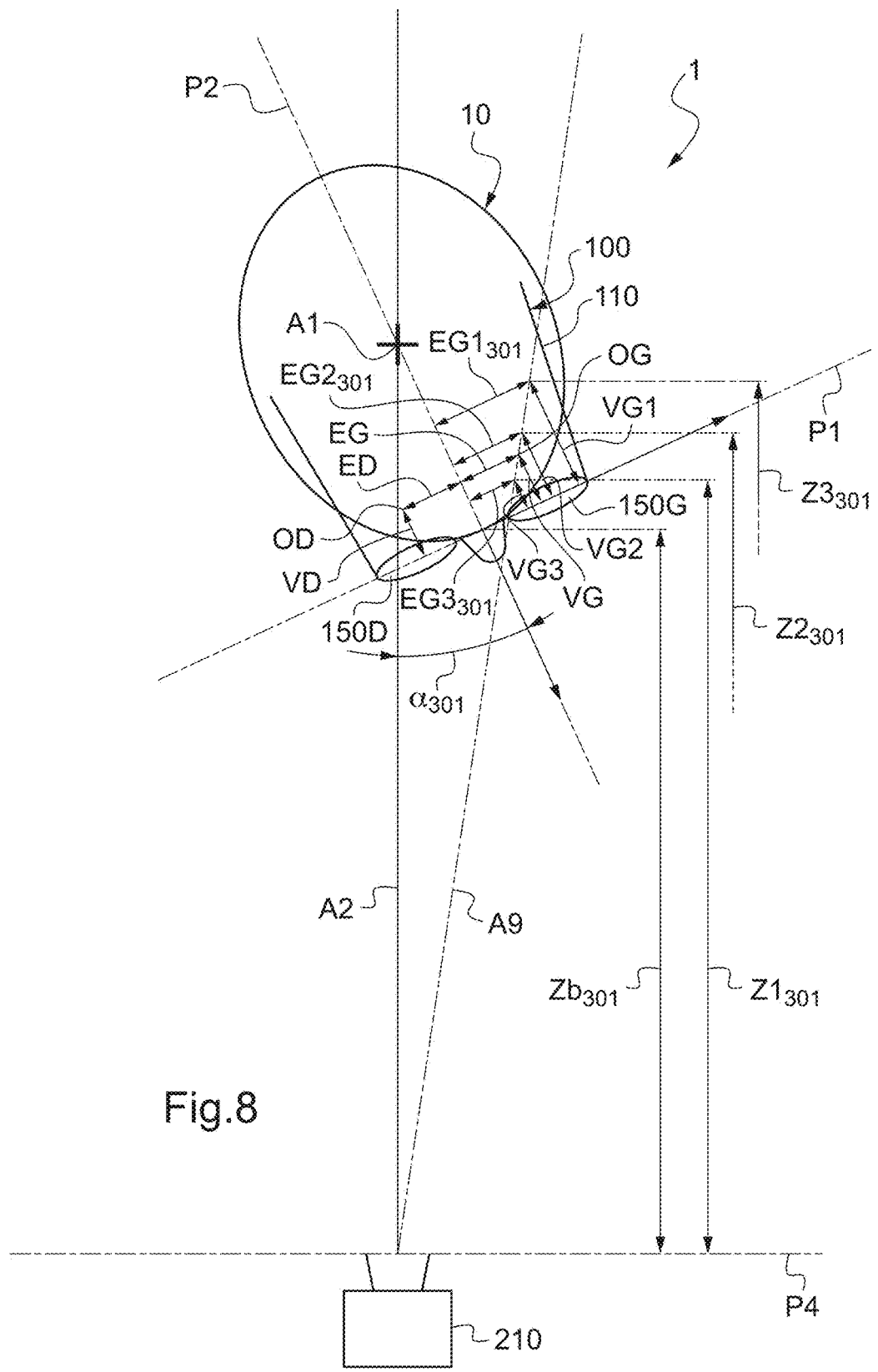
FIG. 8 is a schematic top view of the head of the spectacle wearer in FIG. 1.

Here, as shown in FIG. 8, it will be implemented on the left eye 20G of the wearer 1 in order to determine his or her semi-pupillary distance EG and his or her left eye/spectacles distance VG.

Generally, the statistical procedure is based on the observation that, by virtue of the left corneal reflection 162G appearing in each image 301, 302, 303, the axis A9 (see FIG. 8) on which the center of rotation OG of the left eye 20G of the wearer 1 is located is known, and therefore all that remains to be determined is the position of the center of rotation OG on this axis A9.

This statistical procedure will then consist in:
- simulating, in each image 301, 302, 303, a plurality of eye/spectacles distances VG1, VG2, VG3 (here 3 in number in order to make the description and drawings clearer);
- determining the left semi-pupillary distance corresponding to each of these simulated distances (called the "simulated left semi-pupillary distance $EG1_{301}$, $EG2_{301}$, $EG3_{301}$, $EG1_{302}$, $EG2_{302}$, $EG3_{302}$, $EG1_{303}$, $EG2_{303}$, $EG3_{303}$"), then, as a function of all of these simulated left semi-pupillary distances;
- determining which of the simulated eye/spectacles distances VG1, VG2, VG3 is closest to the actual eye/spectacles distance VG of the wearer 1.

More precisely, the calculation unit 250 here considers three predetermined simulated eye/spectacles distances VG1, VG2, VG3 stored in its read-only memory. As a variant, and preferably, it will rather consider a number of simulated eye/spectacles distances higher than 10.

Then, for each of these simulated eye/spectacles distances, and for each of the acquired images (index i, varying in this example from 301 to 303), the calculation unit 250 calculates iteratively (iteration index k varying from 1 to n):

$$Z1_{i,k} = Zb_i + VG1 \cdot \cos(\alpha_i) + EG1_{i,k-1} \cdot \sin(\alpha_i),$$

$$Z2_{i,k} = Zb_i + VG2 \cdot \cos(\alpha_i) + EG2_{i,k-1} \cdot \sin(\alpha_i)$$

$$Z3_{i,k} = Zb_i + VG3 \cdot \cos(\alpha_i) + EG3_{i,k-1} \cdot \sin(\alpha_i), \text{ with:}$$

- $EG1_{i,0}$, $EG2_{i,0}$, $EG3_{i,0}$ fixed arbitrarily at a predetermined value, here chosen to be equal to 32.5 mm;
- $Zb_i$ the distance separating the observable axis A3 and the general plane P4 of the objective of the video camera 210 in each image (and which is easily determinable, taking into account the width of the frame in the image considered relative to its actual width, and the yaw angle $\alpha_i$ of the head of the wearer);
- $Z1_{i,k}$, $Z2_{i,k}$, $Z3_{i,k}$ the distances separating the simulated position from the center of rotation OG of the left eye 20G of the wearer 1 and the general plane P4 of the objective of the video camera 210.

If we denote:
- $x_{OGi}$ and $y_{OGi}$: the coordinates, expressed in pixels, of the center of rotation OG in the image i, relative to the center of this image;
- X, Y, Z: the coordinates, expressed in mm, of the center of rotation OG in the reference system of the video camera; and
- K, the size of a pixel, expressed in mm, for an object located one meter from the plane of the video camera.

Then, the following equations may be written:

$$X1_{i,k} = Z1_{i,k} \cdot K \cdot x_{OGi}$$

$$Y1_{i,k} = Z1_{i,k} \cdot K \cdot y_{OGi}$$

$$Z1_{i,k} = Z1_{i,k}$$

$$X2_{i,k} = Z2_{i,k} \cdot K \cdot x_{OGi}$$

$$Y2_{i,k} = Z2_{i,k} \cdot K \cdot y_{OGi}$$

$$Z2_{i,k} = Z2_{i,k}$$

$$X3_{i,k} = Z3_{i,k} \cdot K \cdot x_{OGi}$$

$$Y3_{i,k} = Z3_{i,k} \cdot K \cdot y_{OGi}$$

$$Z3_{i,k} = Z3_{i,k}$$

For the image i, the sagittal plane, denoted $P2_i$, may for example be defined as the plane that includes the following three points:
- $A_i$: a point located on the observable axis A3, corresponding to the center of the segment connecting the two closest upper corners of the two boxing-system boxes 151G, 151D;
- $B_i$: a point located on the observable axis A3, corresponding to the center of the segment connecting the two closest lower corners of the two boxing-system boxes 151G, 151D;
- $C_i$: a point located on an axis that passes through the point $A_i$, that is perpendicular to the midplane P1 of the spectacle frame 110, and the coordinates of which in the reference system of the frame are such that the vector $A_iC_i$ has coordinates ($x_c$, $y_c$, $z_c$) where $x_c = 0$ and $y_c = 0$.

If we denote:
- ($x_{Ai}$, $y_{Ai}$) the coordinates of the point $A_i$ in the image i;
- $X_{Ai}$, $Y_{Ai}$, $Z_{Ai}$, the coordinates of the point $A_i$ in the reference system of the video camera;
- ($x_{Bi}$, $y_{Bi}$) the coordinates of the point $A_i$ in the image i;
- $X_{Bi}$, $Y_{Bi}$, $Z_{Bi}$, the coordinates of the point $B_i$ in the reference system of the video camera;
- $X_{Ci}$, $Y_{Ci}$, $Z_{Ci}$, the coordinates of the point $C_i$ in the reference system of the video camera; and
- $M_i$, the three-dimensional rotation matrix describing the attitude of the frame in the space of the video camera (constructed from the angles $\alpha$, $\beta$ and $\delta$).

Then, as the distance of the observable axis A3 to the plane of the video camera P4 is known, $Z_{Ai}$ and $Z_{Bi}$ are known and the following equations may be written:

$$X_{Ai} = Z_{Ai} \cdot K \cdot x_{Ai}$$

$$Y_{Ai} = Y_{Ai} \cdot K \cdot y_{Ai}$$

$$X_{Bi} = Z_{Bi} \cdot K \cdot x_{Bi}$$

$$Y_{Bi} = Y_{Bi} \cdot K \cdot y_{Bi}$$

And, after inversion of the rotation matrix M:

$$(X_{Ci}-X_{Ai})=M^{-1}(0,0)\cdot x_c+M^{-1}(0,1)\cdot y_c+M^{-1}(0,2)\cdot z_c$$

$$(Y_{Ci}-Y_{Ai})=M^{-1}(1,0)\cdot x_c+M^{-1}(1,1)\cdot y_c+M^{-1}(1,2)\cdot z_c$$

$$(Z_{Ci}-Z_{Ai})=M^{-1}(2,0)\cdot x_c+M^{-1}(2,1)\cdot y_c+M^{-1}(2,2)\cdot z_c$$

As $x_c$ and $y_c$ are equal to zero by definition, it may be deduced therefrom that:

$$X_{Ci}=X_{Ai}+M^{-1}(0,2)\cdot z_c$$

$$Y_{Ci}=Y_{Ai}+M^{-1}(1,2)\cdot z_c$$

$$Z_{Ci}=Z_{Ai}+M^{-1}(2,2)\cdot z_c$$

Since the coordinates of the 3 points of the plane $P2_i$ are known, the latter is perfectly defined, and it is therefore possible to calculate using the conventional procedure the distance of any point in the plane $P2_i$.

In particular $EG1_{i,k}$, $EG2_{i,k}$ and $EG3_{i,k}$ may therefore be calculated, with:
- $EG1_{i,k}$: the distance separating the center of rotation OG from the plane $P2_i$, taking into account the eye/spectacles distance VG1;
- $EG2_{i,k}$: the distance separating the center of rotation OG from the plane $P2_i$, taking into account the eye/spectacles distance VG2;
- $EG3_{i,k}$: the distance separating the center of rotation OG from the plane $P2_i$, taking into account the eye/spectacles distance VG3.

These values may then be reinserted into the initial formulae in order to continue the iteration.

The iterative calculation stops either after a predetermined number of iterations (for example k=3), or when for two successive iterations the values of $EG1_{i,k}$ and $EG1_{i,k+1}$, those of $EG2_{i,k}$ and $EG2_{i,k+1}$ and those of $EG3_{i,k}$ and $EG3_{i,k+1}$ are close (namely here less than 0.1 mm).

The values of $EG1_{i,k}$, $EG2_{i,k}$, $EG3_{i,k}$ obtained are then considered as being the simulated semi-pupillary distances $EG1_i$, $EG2_i$, $EG3_i$.

Once all of the simulated semi-pupillary distances $EG1_i$, $EG2_i$, $EG3_i$ have been calculated, the calculation unit 250 selects, from the simulated eye/spectacles distances VG1, VG2, VG3, the distance that is closest to the actual value VG.

To do this, the calculation unit 250 determines, for each simulated eye/spectacles distance VG1, VG2, VG3, the standard deviation $\sigma_1$, $\sigma_2$, $\sigma_3$ of the associated simulated semi-pupillary distances $EG1_i$, $EG2_i$, $EG3_i$.

By way of example, the standard deviation $\sigma_1$ associated with the first simulated eye/spectacles distance VG1 is equal to the standard deviation of the simulated semi-pupillary distances $EG1_{303}$, $EG1_{302}$, $EG1_{303}$.

Thus, the selected simulated eye/spectacles distance VG2 is that for which the standard deviation $\sigma_2$ is the lowest.

The calculation unit 250 then considers that this simulated eye/spectacles distance VG2, once scaled, is equal to the actual eye/spectacles distance VG of the wearer 1. It therefore stores its value in memory.

The calculation unit 250 then calculates the average of the simulated semi-pupillary distances $EG2_{301}$, $EG2_{302}$, $EG2_{303}$ associated with this selected simulated value VG2.

It then considers that this average, once scaled, is equal to the left semi-pupillary distance EG of the wearer 1. It therefore stores its value in memory.

The right eye/spectacles distance VD and the right semi-pupillary distance ED of the wearer 1 may then be determined in the same way as for the left eye/spectacles distance VG and the left semi-pupillary distance EG of the wearer 1.

In a subsequent operation, the calculation unit 250 calculates the pupillary heights HG, HD of the wearer 1 (see FIG. 1).

Once again, the calculation unit 250 may proceed in various ways.

Here, the pitch of the head 10 of the wearer 1 is considered to have little impact on the precision of the pupillary heights HG, HD that may be measured in the images 301, 302, 303.

Therefore, to determine these pupillary heights, the calculation unit 250 selects any one of the images 301, 302, 303 (for example that for which the yaw angle $\alpha_{302}$ is the smallest) then determines in this image 302 (FIG. 6) the distances $HG_{302}$, $HD_{302}$ separating each of the corneal reflections 162G, 162D from the lower edge of the corresponding boxing-system box 151G, 151D.

These distances $HG_{302}$, $HD_{302}$, once scaled, are then stored in memory by the calculation unit 250 as being the pupillary heights HG, HD.

As a variant, the calculation unit will possibly measure these distances $HG_i$, $HD_i$ in each of the images 301, 302, 303, average these distances and scale them in order to obtain the pupillary heights of the wearer.

As another variant, the pupillary heights will possibly be calculated using a method analogous to that used to determine the semi-pupillary distances of the wearer. This method will for example consist in acquiring various images of the wearer nodding their head to say "yes", in determining the pitch angles of the head in each of these images, and in measuring the pupillary heights in the image for which the pitch angle is smallest.

The following operation consists, for the calculation unit 250, in determining the propensity of the wearer 1 to turn their gaze by moving rather their head 10 or their eyes 20G, 20D.

The vendor then explains to the wearer 1 that he or she must look at the first additional target 320, then, once the latter is turned off and the second additional target 330 is turned on, that he or she must rapidly turn their gaze toward this second additional target 330.

Once the wearer 1 is ready, the vendor initiates a new series of measurements by pressing on an ad hoc button displayed on the touchscreen 270.

The calculation unit 250 then turns on only the first additional target 320, for about 5 seconds, then turns off the first additional target 320 and simultaneously turns on the second additional target 330. At the moment when the first additional target 320 is turned off, the calculation unit 250 acquires and stores in memory a plurality of images (10 for example) during a sequence of about one second.

The acquired images are then processed by the calculation unit 250 in order to determine, in each of them, the yaw angle $\alpha_i$ of the head 10 of the wearer 1.

If, in the 10 acquired images, this angle varies little and/or slowly, the calculation unit 250 determines that the wearer has a propensity to turn their gaze by moving rather their eyes 20G, 20D.

On the other hand, if, in the 10 acquired images, this angle varies a lot and/or rapidly, the calculation unit 250 determines that the wearer has a propensity to turn their gaze by moving rather their head 10.

As a variant, the calculation unit could proceed in another way.

By way of example, a more refined approach could be used, the distances $EG_i$, $ED_i$ separating the corneal reflections 162D, 162G from the observable axis A3 also being determined in each acquired image.

It could then compare the speeds and/or amplitudes of variation in the yaw angle $\alpha_i$ with the speeds and/or amplitudes of variation in the distances $EG_i$, $ED_i$. It could thus deduce therefrom whether the wearer has a propensity to turn their eyes or head more rapidly. It could even deduce therefrom a refined coefficient, quantifying the propensity of the wearer to turn their gaze by moving rather their head or their eyes.

Following these various operations, the calculation unit 250 has acquired:
- a scanned image of the prescriptions of the wearer;
- the model of the spectacle frame selected by the wearer 1;
- the semi-pupillary distances EG, ED of the wearer 1;
- the pupillary heights HG, HD of the wearer 1;
- a visible image of the face of the wearer 1;
- the distances VG2, VD2 separating the centers of rotation of the eyes of the wearer 1 and the midplane P1 of the spectacle frame 110; and
- a coefficient quantifying the propensity of the wearer 1 to turn their gaze by moving rather their head 10 or their eyes 20G, 20D.

It then displays these various pieces of information on the touchscreen 270 so that they can be verified by the vendor.

After validation by the vendor, the calculation unit 250 has this information printed on a summarizing sheet. The calculation unit then communicates this information to the center for manufacturing ophthalmic lenses.

Optionally, provision will possibly be made for the calculation unit 250 to furthermore communicate all of the acquired images to the center for manufacturing ophthalmic lenses.

Thus, the processing center will optionally be able to carry out an operation for verifying all the data calculated by the calculation unit 250.

These data will possibly be verified in particular when the software package installed in the calculation unit 250 is not up-to-date.

They will also possibly be verified when the selected frame is a "rimless" frame. This is because the edges of the demonstration lenses of these frames are generally difficult to see in the acquired images, which may generate errors.

This verifying operation will possibly be carried out automatically (especially in the case where the software package is not up-to-date), or manually, by a specialist technician who will possibly in particular verify that the pupils and the edges of the demonstration lenses have been correctly pinpointed.

The present invention is in no way limited to the embodiments described and shown, and those skilled in the art will be able to make modifications thereto without departing from the scope of the invention.

In particular, provision will possibly be made for the measuring device to take, rather than the form of a kiosk housing the calculation unit, the image sensor and the light sources, a smaller, portable form. Thus, provision will possibly be made for the calculation unit to be formed by a portable computer in which an ad hoc software package will be installed, and the video camera (or "web-cam") of which will play the role of the video camera in the visible domain. In this variant, the infrared video camera and the light source will then be arranged in a small housing equipped with a clip for fastening to the screen of the portable computer and a cable for connecting to the portable computer. This solution will be inexpensive and easily transportable.

According to another variant embodiment of the invention, provision will possibly be made for the calculation unit to merely capture images and communicate them to the center for manufacturing ophthalmic lenses, in which case these images will be processed in this manufacturing center.

The invention claimed is:

1. A method for estimating an eye/spectacles distance, between a characteristic plane of a pair of spectacles and a characteristic point of an eye of a wearer of said pair of spectacles, with the help of a determination device comprising an image sensor and a calculation unit, the method comprising steps:
   a) of acquisition by the image sensor of at least two distinct images of at least one part of the head of the wearer, in which the head of the wearer exhibits various angular positions with respect to the image sensor around a pivoting axis which is substantially parallel to said characteristic plane and which is substantially transverse to the optical axis of the image sensor,
   b) of determination, for each image acquired, of an angle of inclination of the head of the wearer with respect to the image sensor, measured between the optical axis of the image sensor and a plane tied to the head of the wearer which is substantially parallel to said pivoting axis and substantially orthogonal to said characteristic plane,
   c) of acquisition of at least two predetermined simulated values of the eye/spectacles distance sought stored in read-only memory of the calculation unit,
   d) of calculation, for each image acquired and with each simulated value acquired, of a morphological distance between the characteristic point of the eye of the wearer and the plane tied to the head of the wearer, as a function of said angle of inclination, and
   e) of selection, from among the simulated values of the eye/spectacles distance sought, of the value closest to the eye/spectacles distance of the wearer, as a function of the head/plane distances calculated in step d).

2. The estimating method as claimed in claim 1, in which, in step a), said pivoting axis coincides with the longitudinal axis of the head of the wearer, and in step b), the plane tied to the head of the wearer is parallel to the sagittal plane of the head of the wearer and said angle of inclination is an angle of yaw.

3. The estimating method as claimed in claim 2, in which the characteristic point of the head of the wearer is the center of rotation of one of the two eyes of the wearer, the plane tied to the head of the wearer coincides with the sagittal plane of the head of the wearer, and each morphological distance calculated in step d) is an assumed semi-pupillary distance of the wearer calculated as a function of the position in the image acquired of the position of a corneal reflection reflected by the cornea of said eye of the wearer.

4. The estimating method as claimed in claim 1, in which the position of the plane tied to the head of the wearer is obtained by pinpointing the position of the pair of spectacles in each of the images acquired.

5. The estimating method as claimed in claim 4, in which, in step e),
   for each simulated value, a rate of dispersion of the morphological distances associated with this simulated value is determined, and
   the simulated value selected is that for which the morphological distances are the least dispersed.

6. The estimating method as claimed in claim 5, in which the rate of dispersion of the morphological distances is a standard deviation.

7. The estimating method as claimed in claim 5, comprising an additional step of estimating the semi-pupillary distance of the wearer, in the course of which the average of the morphological distances associated with the simulated value selected is calculated.

8. The estimating method as claimed in claim 1, in which, the device further comprises a light source, and in step b), said angle of inclination is determined as a function of the position, in each image, of the reflections generated by the light source and reflected by the two lenses of the pair of spectacles.

9. The estimating method as claimed in claim 8, in which said light source is infrared and said image sensor acquires infrared images.

10. The estimating method as claimed in claim 1, in which the characteristic plane of the pair of spectacles is substantially parallel to the midplane of the contours of the lenses of the pair of spectacles.

11. The estimating method as claimed in claim 1, in which said angle of inclination is obtained by installing on the pair of spectacles a pinpointing element having a known geometry, and by determining the position and the shape of said pinpointing element in each image acquired.

12. The estimating method as claimed in claim 1, in which a dimension characteristic of said pair of spectacles is acquired and in which said eye/spectacles distance of the wearer is scaled as a function of said characteristic dimension acquired.

13. A device for estimating an eye/spectacles distance, between a characteristic plane of a pair of spectacles and a characteristic point of a head of a wearer of said pair of spectacles, which comprises:

at least one light source positioned for illuminating the head of the wearer, an image sensor exhibiting an optical axis directed substantially toward the head of the wearer and positioned for acquiring at least two images of the head of the wearer in which the pair of spectacles illuminated by the light source appears and in which the head of the wearer exhibits distinct inclinations around a pivoting axis substantially parallel to said characteristic plane and transverse to the optical axis of the image sensor, and a calculation unit connected for processing said images, wherein said calculation unit is configured and operated for:

determining, for each image acquired, an angle of inclination of the head of the wearer with respect to the image sensor, measured between the optical axis of the image sensor and a plane tied to the head of the wearer which is substantially parallel to said pivoting axis and substantially orthogonal to said characteristic plane, acquiring at least two predetermined simulated values of the eye/spectacles distance sought stored in read-only memory of the calculation unit, calculating, for each image acquired and with each simulated value acquired, a morphological distance between the characteristic point of the head of the wearer and the plane tied to the head of the wearer, as a function of said angle of inclination, and selecting, from among the simulated values of the eye/spectacles distance sought, the value closest to the eye/spectacles distance of the wearer, as a function of the head/plane distances calculated.

* * * * *